(12) United States Patent
Zhang et al.

(10) Patent No.: US 11,883,464 B2
(45) Date of Patent: *Jan. 30, 2024

(54) NERVE GROWTH FACTOR FUSION PROTEIN, PREPARATION METHOD AND USE THEREOF

(71) Applicant: Staidson (Beijing) Biopharmaceuticals Co., Ltd., Beijing (CN)

(72) Inventors: Qingshuang Zhang, Beijing (CN); Lei Ma, Beijing (CN); Ming Liu, Beijing (CN)

(73) Assignee: Staidson (Beijing) Biopharmaceuticals Co., Ltd., Beijing (CN)

( * ) Notice: Subject to any disclaimer, the term of this patent is extended or adjusted under 35 U.S.C. 154(b) by 69 days.

This patent is subject to a terminal disclaimer.

(21) Appl. No.: 16/085,984

(22) PCT Filed: Mar. 17, 2017

(86) PCT No.: PCT/CN2017/077025
§ 371 (c)(1),
(2) Date: Sep. 17, 2018

(87) PCT Pub. No.: WO2017/157325
PCT Pub. Date: Sep. 21, 2017

(65) Prior Publication Data
US 2020/0331977 A1  Oct. 22, 2020

(30) Foreign Application Priority Data

Mar. 18, 2016 (CN) .......................... 201610159303.7

(51) Int. Cl.
| | | |
|---|---|---|
| *C07K 14/48* | (2006.01) | |
| *A61K 38/00* | (2006.01) | |
| *A61P 25/00* | (2006.01) | |
| *A61K 38/18* | (2006.01) | |
| *C12N 15/85* | (2006.01) | |

(52) U.S. Cl.
CPC ............ *A61K 38/18* (2013.01); *A61K 38/185* (2013.01); *A61P 25/00* (2018.01); *C07K 14/48* (2013.01); *C12N 15/85* (2013.01); *A61K 38/00* (2013.01); *C07K 2319/30* (2013.01)

(58) Field of Classification Search
CPC .... C07K 14/48; C07K 15/85; C07K 2319/30; A61K 38/18; A61K 38/185; A61P 25/00; A61P 25/02
See application file for complete search history.

(56) References Cited

U.S. PATENT DOCUMENTS

| | | |
|---|---|---|
| 5,349,055 A | 9/1994 | Persson et al. |
| 7,452,863 B1 | 11/2008 | Presta et al. |
| 7,935,671 B2 | 5/2011 | Urfer et al. |
| 8,101,571 B2 | 1/2012 | Presta et al. |
| 2012/0230990 A1 | 9/2012 | Beckmann et al. |
| 2019/0105373 A1 | 4/2019 | Wang et al. |

FOREIGN PATENT DOCUMENTS

| | | |
|---|---|---|
| CN | 1079992 A | 12/1993 |
| CN | 1698883 A | 11/2005 |
| CN | 102665759 A | 9/2012 |
| CN | 103159843 A | 6/2013 |
| CN | 105273087 A | 1/2016 |
| WO | WO 2008/006893 A1 | 1/2008 |
| WO | WO 2009/080823 A2 | 7/2009 |

OTHER PUBLICATIONS

Peppel et al. A tumor necrosis factor (TNF) receptor-IgG heavy chain chimeric protein as a bivalent antagonist of TNF activity. J Exp Med. Dec. 1, 1991;174(6):1483-9.*
Rath et al. Fc-fusion proteins and FcRn: structural insights for longer-lasting and more effective therapeutics. Critical Reviews in Biotechnology vol. 35, 2015—Issue 2, pp. 235-254, Published online: Oct. 24, 2013.*
Capsoni, Simona et al., "Taking Pain Out of NGF: A "Painless" NGF Mutant, Linked to Hereditary Sensory Autonomic Neuropathy Type V, with Full Neurotrophic Activity" PLoS One, Feb. 2011, pp. 1-12, vol. 6, Issue 2, e17321.
Niranjana, K.R.P. et al., "Fc IgG1 heavy chain constant region, partial [*Homo sapiens*]" GenBank Accession ID: AEV43323. 1, Dec. 11, 2011.
Urfer, Roman et al., "The binding epitopes of neurotrophin-3 to its receptors trkC and gp75 and the design of a multifunctional human neurotrophin" The EMBO Journal, 1994, pp. 5896-5909, vol. 13, No. 24.
Wiesmann, C. et al., "Nerve growth factor: structure and function" CMLS, Cellular and Molecular Life Sciences, 2001, pp. 748-759, vol. 58.
International Search Report for PCT/CN2017/077025 dated Jun. 15, 2017.
Written Opinion for PCT/CN2017/077025 dated Jun. 15, 2017.
Fukui, Yu et al., "Low Affinity NGF Receptor (p75 Neurotrophin Receptor) Inhibitory Antibody Reduces Pain Behavior and CGRP Expression in DRG in the Mouse Sciatic Nerve Crush Model" Journal of Orthopaedic Research, Mar. 2010, pp. 279-283.

(Continued)

*Primary Examiner* — Gregory S Emch
*Assistant Examiner* — Aditi Dutt
(74) *Attorney, Agent, or Firm* — Knobbe Martens Olson & Bear LLP

(57) ABSTRACT

The present disclosure relates to the field of biopharmaceuticals and provides a nerve growth factor (NGF) fusion protein and a preparation method and use thereof. The fusion protein has a general formula represented by A-B or A-L-B, wherein A is a nerve growth factor, L is a linker peptide, and B is an Fc moiety of IgG, or an analogue of the Fc moiety of IgG, or a fragment of the Fc moiety of IgG. The fusion protein of the present disclosure has the following advantages over a wild-type NGF: higher biological activity, a half-life extended more than 17 times, greatly reduced administration frequency, and significantly increased efficacy.

9 Claims, 2 Drawing Sheets
Specification includes a Sequence Listing.

(56) References Cited

OTHER PUBLICATIONS

Rydén, Mikael et al., "A Second Determinant of Binding to the p75 Neurotrophin Receptor Revealed by Alanine-scanning Mutagenesis of a Conserved Loop in Nerve Growth Factor" The Journal of Biological Chemistry, Dec. 1997, pp. 33085-33091, vol. 272, No. 52.

Supplementary European Search Report for EP 17765867 dated Jul. 4, 2019.

Supplementary Partial European Search Report for EP 17765868 dated Aug. 9, 2019.

Saxena et al., "Advances in Therapeutic Fc Engineering—Modulation of IgG—Associated Effector Function and Serum Half-life", Frontiers in Immunology, vol. 7, Article 580, Dec. 12, 2016.

Borrok et al., "An "Fc-Silenced" IgG1 Format With Extended Half-Life Designed for Improved Stability", Journal of Pharmaceutical Sciences, 106, 2017, pp. 1008-1017.

Dumet et al., "Insights into the IgG heavy chain engineering patent landscape as applied to IgG4 antibody development", MABS, vol. 11, No. 8, 2019, pp. 1341-1350.

Van der Horst et al., "Fc-Engineered Antibodies with Enhanced Fc-Effector Function for the Treatment of B-Cell Malignancies", Cancers 2020, 12, 3041.

Shields et al., "Lack of Fucose on Human IgG1 N-Linked Oligosaccharide Improves Binding to Human FcγRIII and Antibody-dependent Cellular Toxicity", The Journal of Biological Chemistry by the American Society for Biochemistry and Molecular Biology, Inc., vol. 277, No. 30, Jul. 26, 2002, pp. 26733-26740.

Lazar et al., "Engineered antibody Fc variants with enhanced effector function", PNAS, vol. 103, No. 11, Mar. 14, 2006, pp. 4005-4010.

Masuda et al., "Enhanced binding affinity for FcγRIIIa of fucose-negative antibody is sufficient to induce maximal antibody-dependent cellular cytotoxicity", Molecular Immunology 44, 2017, pp. 3122-3131.

Liu et al., "Asymmetrical Fc Engineering Greatly Enhances Antibody-dependent Cellular Cytotoxicity (ADCC) Effector Function and Stability of the Modified Antibodies", The Journal of Biological Chemistry, vol. 289, No. 6, Feb. 7, 2014, pp. 3571-3590.

Ullrich, Axel et al., "Human β-nerve growth factor gene sequence highly homologous to that of mouse" Nature, Jun. 1983, pp. 821-825, vol. 303.

\* cited by examiner

NERVE GROWTH FACTOR FUSION PROTEIN, PREPARATION METHOD AND USE THEREOF

CROSS REFERENCE TO RELATED APPLICATIONS

This application is a U.S. National Phase Application of PCT International Application Number PCT/CN2017/077025, filed on Mar. 17, 2017, designating the United States of America and published in the Chinese language, which is an International Application of and claims the benefit of priority to Chinese Patent Application No. 201610159303.7, filed on Mar. 18, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is RevisedSeqList-DRGN005-001APC.txt, the date of creation of the ASCII text file is Apr. 24, 2023, and the size of the ASCII text file is 44 KB.

TECHNICAL FIELD

The disclosure relates to a nerve growth factor fusion protein, a preparation method and use thereof, and belongs to the field of biopharmaceutics.

BACKGROUND

Nerve Growth Factor (NGF) is the first neurotrophic factor discovered in mouse sarcoma cells by Italian scientist Levi-Monticini in 1953. NGF is a neuronal growth regulator having a dual biological function of neuron nutrition and promoting neurite growth, which plays an important regulatory role in the development, differentiation, growth, regeneration, and expression of functional properties of central and peripheral neurons. NGF includes three subunits of α, β, and γ. The β subunit is an active region, which is formed by combining two single chains through a non-covalent bond. At present, a number of NGF products have been marketed at home and abroad, and are mainly used for the treatment of nervous system dysplasia, including amblyopia, neuroma, various nerve injuries and nervous system diseases.

As a protein drug, activity of NGF promoting nerve growth is mainly in a β-NGF having a sedimentation coefficient of 2.5S, a molecular weight of 13.5 Kd and being easily filtered by glomerulus during metabolism, resulting in a short half-life in vivo. Studies have shown that mice were intramuscularly administered with β-NGF drug, T1/2 (β)=2.2 h, Tmax=0.5 h, and the frequency of injection was once a day. Due to the adverse reactions of a pain at the injection site or in the lower limb on the injection side during an NGF injection, the reduction in the number and frequency of administration to the patient is good for alleviating the adverse reactions of the patient. One of the solutions is to develop a long-acting and high biologically active NGF.

Protein drug modification is one of the research focuses on a long acting of current protein drugs, in which the construction of fusion proteins is an important strategy for protein modification. A gene of the target protein is linked end-to-end with a gene of a certain protein having a longer half-life and larger molecular weight, and the gene expression product (i.e., the fusion protein) is controlled by the same regulatory sequence, but it is still a clinically difficult problem to increase the biological activity of the protein drug while prolonging its half-life.

SUMMARY

In order to solve the above problems, an object of the present application is to provide a nerve growth factor fusion protein. As compared with an original protein, the fusion protein not only has an enhanced biological activity, greatly prolonged half-life and reduced the number and frequency of administration to patients, thereby alleviating the patient's adverse reactions, but also has significantly improved the efficacy.

The present application provides a nerve growth factor fusion protein, represented by a general formula A-B or A-L-B, in which A is a nerve growth factor, L is a linker peptide, and B is an Fc moiety of IgG, an analogue of the Fc moiety of IgG, or a fragment of the Fc moiety of IgG.

IgG is an immunoglobulin having the highest content in serum. IgG is also an immunoglobulin having the longest half-life in serum among all immunoglobulins. Unlike other immunoglobulins, IgG may efficiently recycle after binding to an Fc receptor. There are four subclasses of IgG, i.e., G1, G2, G3, and G4, each having different effector functions. The Fc moiety of an immunoglobulin used herein has the common meaning of terms in the field of immunology. Specifically, the term "Fc moiety of an immunoglobulin" refers to an antibody fragment obtained by removing two antigen binding regions (Fab fragments) from an antibody. One method for removing Fab fragments is to digest the immunoglobulin with papain. Thus, the Fc moiety is formed by fragments having almost equal size of the constant regions of two heavy chains, in which the two heavy chains are associated by a non-covalent interactions and a disulfide bond. The Fc moiety may include a hinge region and extends through CH2 and CH3 domains to the C-terminal of the antibody.

According to the desired effect in vivo, the B moiety in the general formula of the nerve growth factor fusion protein may be an Fc moiety of any subclass of IgG or a mutant thereof. Thus, the nerve growth factor fusion protein of the present application may include an intact Fc moiety of an immunoglobulin, a fragment of the Fc moiety of the immunoglobulin, or an analog thereof, that is fused to a nerve growth factor.

Due to the introduction of a sequence of the Fc moiety, it may affect the activity of NGF, and may also mediate antibody-dependent cytotoxicity and complement-dependent cytotoxicity. Therefore, in order to obtain a fusion protein having a high biological activity and a long half-life, it is necessary to screen or mutate the Fc sequences of various subclasses.

B in the general formula of the nerve growth factor fusion protein is an Fc moiety of IgG1, an analog of the Fc moiety of IgG1, or a fragment of the Fc moiety of IgG1; preferably, the Fc moiety of IgG1 includes CH2 and CH3 regions, including a hinge region; and more preferably, the Fc moiety of IgG1 has an amino acid sequence of SEQ ID NO: 5.

Preferably, B in the nerve growth factor fusion protein is preferably an analog of the Fc moiety of IgG1. The analog of the Fc moiety includes an engineering modification, and the engineering modification may be a site mutation associated with antibody dependent cell-mediated cytotoxicity (ADCC)/complement dependent cytotoxicity (CDC) activity, or a deglycosylation mutation. More preferably, the analog of the Fc moiety has an amino acid sequence of SEQ ID NO: 7. Further preferably, the analog of the Fc moiety has an amino acid sequence of SEQ ID NO: 7 with the first 5 amino acids deleting at N-terminal.

The nerve growth factor is a wild type human nerve growth factor. Any human nerve growth factor may be a part of the nerve growth factor fusion protein of the present application, as long as the human nerve growth factor itself may bind to the human nerve growth factor receptor and induces a signal transmission through the human nerve growth factor receptor.

The nerve growth factor is an analog of a human nerve growth factor, and generally preferably a human nerve growth factor having no more than 6 amino acid mutation sites, even more preferably, a human nerve growth factor having no more than 5 amino acid mutation sites, and most preferably a human nerve growth factor having no more than 4, 3 or 2 amino acid mutation sites.

The human nerve growth factor is a derivative of a human nerve growth factor. The term "a derivative of a human nerve growth factor" herein refers to a molecule having an amino acid sequence of a human nerve growth factor or an analog of the human nerve growth factor, but also having an additional chemical modification at one or more of amino acid side groups, alpha carbon atoms, terminal amino groups or terminal carboxyl groups. The chemical modifications include, but are not limited to, adding chemical moieties, creating new bonds, and removing chemical moieties. The modification at amino acid side groups includes, but is not limited to, an acylation of an epsilon amino group of lysine, an N-alkylation of arginine, histidine or lysine, an alkylation of carboxyl of glutamic acid or aspartic acid, and a deamination of glutamine or asparagine. The modification at terminal amino groups includes, but is not limited to, deamination, N-lower alkyl, N-di-lower alkyl, and N-acyl modifications. The modification at terminal carboxyl groups includes, but is not limited to, amide, lower alkyl acyl, dialkyl amide, and lower alkyl ester modifications. The lower alkyl group is a C1-C4 alkyl group. In addition, one or more side groups or terminal groups may be protected by a protecting group known to a person skilled in the field of chemistry. An alpha carbon of an amino acid may be mono- or di-methylated.

Many active fragments, analogs and derivatives of the human nerve growth factor are well known in the art, and any one of these analogs and derivatives may be a part of the nerve growth factor fusion protein of the present application. Some examples of new analogs of the human nerve growth factor as well as analogs and derivatives of the human nerve growth factor well known in the art are provided herein.

The human nerve growth factor has preferably an amino acid sequence of any one of SEQ ID NO: 1, SEQ ID NO: 2, SEQ ID NO: 13 to SEQ ID NO: 30 in the sequence listing.

The human nerve growth factor of the present application includes a series of nerve growth factor mutants (i.e., recombinant hNGFs), which are capable of alleviating side effects such as pain and are even painless. These nerve growth factor mutants have an amino acid sequence of any one of SEQ ID NO: 2 and SEQ ID NO: 13 to SEQ ID NO: 30 in the sequence listing, respectively.

F12E: has an amino acid sequence of SEQ ID NO: 2 (i.e., the F12E substitution corresponds to F133E as set forth in SEQ ID NO: 2);
K32G: has an amino acid sequence of SEQ ID NO: 13;
K32L: has an amino acid sequence of SEQ ID NO: 14;
K32Y: has an amino acid sequence of SEQ ID NO: 15;
R59L: has an amino acid sequence of SEQ ID NO: 16;
R59A: has an amino acid sequence of SEQ ID NO: 17;
D65A: has an amino acid sequence of SEQ ID NO: 18;
D65G: has an amino acid sequence of SEQ ID NO: 19;
K74L: has an amino acid sequence of SEQ ID NO: 20;
K88F: has an amino acid sequence of SEQ ID NO: 21;
K88L: has an amino acid sequence of SEQ ID NO: 22;
K88E: has an amino acid sequence of SEQ ID NO: 23;
K88G: has an amino acid sequence of SEQ ID NO: 24;
Q96E: has an amino acid sequence of SEQ ID NO: 25;
R114V: has an amino acid sequence of SEQ ID NO: 26;
R114F: has an amino acid sequence of SEQ ID NO: 27;
R114G: has an amino acid sequence of SEQ ID NO: 28;
R114L: has an amino acid sequence of SEQ ID NO: 29; and
F101A: has an amino acid sequence of SEQ ID NO: 30.

L is a glycine-rich peptide or a peptide having a sequence [SEQ ID NO: 46]n, in which n is 1, 2, 3, 4, 5 or 6. Preferably, the function and stability in vivo of the nerve growth factor fusion protein of the present application is optimized by the addition of a linker peptide (L in the general formula) to prevent potential undesired domain interactions. Although these linker peptides may be of any length and consist of any combination of amino acids, and their lengths preferably do not exceed the length necessary to prevent undesired domain interactions and/or to optimize biological function and/or stability. The linker peptide is preferably enriched in serine-glycine, and preferably is not more than 30 amino acids in length. The linker peptide is more preferably not more than 20 amino acids in length, and more preferably not more than 15 amino acids in length. A preferred linker peptide includes a repetition of the sequence SEQ ID NO: 46. Preferably, there are 2 to 6 repetitions of this sequence. Even more preferably, there are 3 to 4 repetitions of this sequence. The most preferred sequence of the linker peptide is SEQ ID NO: 47. That is, the most preferred linker peptide L is [SEQ ID NO: 46]$_3$.

Preferably, the nerve growth factor fusion protein has an amino acid sequence of SEQ ID NO: 10.

The present application also encompasses a polynucleotide sequence, encoding the above-mentioned nerve growth factor fusion protein.

An expression vector includes the nucleotide sequence.

The expression vector is a DNA vector or a viral vector.

The DNA vector is selected from the group consisting of a DNA plasmid vector, a liposome bound thereto, a molecular conjugate bound thereto, and a polymer bound thereto; and preferably, the DNA plasmid vector is a eukaryotic expression vector; and the viral vector is selected from the group consisting of an adeno-associated virus vector, a lentiviral vector and an adenoviral vector.

A method for preparing a nerve growth factor fusion protein includes: transforming the above-mentioned expression vector into a host cell, and culturing a resultant recombinant cell to express the expression vector, so as to obtain the nerve growth factor fusion protein.

A host cell includes the expression vector.

The host cell is a mammalian cell.

The mammalian cell is a Chinese hamster ovary cell, a human embryonic kidney 293 cell, a COS cell or a Hela cell.

Provided is a pharmaceutical composition, comprising a pharmaceutically acceptable excipient, and one or more of the above-mentioned nerve growth factor fusion protein, the above-mentioned expression vector, and the above-mentioned host cell.

The medicament of the present application may be prepared into various forms such as an injection, a capsule, a tablet or powder, and the medicament having the above various dosage forms may be prepared according to a conventional method in the field of pharmacy.

The pharmaceutical composition is preferably an injection comprising a pharmaceutically acceptable excipient and the above-mentioned nerve growth factor fusion protein.

Provided is use of the nerve growth factor fusion protein in the preparation of a medicament for treating a nervous system disease. The nervous system disease refers to a disease associated with neuronal degeneration or injury in the central and/or peripheral nervous system. Specific examples of the nervous system diseases include, but are not limited to, Alzheimer's disease, Parkinson's disease, Huntington's disease, stroke, ALS, peripheral neuropathy, and other disorders characterized by necrosis or loss of neuron, regardless central neuron, peripheral neuron, or motor neuron, except treating nerve damage caused by trauma, burns, kidney failure, or injury. For example, peripheral neuropathy associated with certain conditions is such as a neuropathy associated with diabetes, AIDS or chemotherapy.

The medicament for treating a nervous system disease prepared by a nerve growth factor fusion protein may be administered to a patient. The exact dosage will depend on the disease to be treated, and may be determined by one skilled in the art using known techniques. Additionally, as is known in the art, an adjustment needs to be made based on age, weight, general health, gender, diet, time of administration, drug interaction, and severity of the disease, and may be determined by one skilled in the art through routine experimentation. The patient mentioned herein includes humans, and other animals and organisms. Therefore, these methods may be used for treating human and livestock.

The administration of the medicament for treating a nervous system disease prepared by the nerve growth factor fusion protein of the present application may be carried out by various methods, including, but not limited to, oral, subcutaneous, intravenous, intracerebral, intranasal, transdermal, intraperitoneal, intramuscular, intrapulmonary, vaginal, rectal, and intraocular administrations. Under some circumstances, such as treating a wound, it may be applied directly in a form of a solution or spray.

The pharmaceutical composition of the present application includes the nerve growth factor fusion protein in a form suitable for administration to a patient. In a preferred example, the pharmaceutical composition is in a water soluble form, and may include, for example, a carrier, a excipient, a stabilizer, a buffer, a salt, an antioxidant, a hydrophilic polymer, an amino acids, a carbohydrate, an ionic or nonionic surfactant, polyethylene glycol, propylene glycol or the like. The medicament prepared by the nerve growth factor fusion protein may also be implanted in a sustained release form by techniques known in the art or embedded in a microcapsule form.

Provided is use of the nerve growth factor fusion protein in the preparation of a medicament for effectively reducing weight.

The present application has the following advantages: as compared with the wild type NGF, the nerve growth factor fusion protein of the present application has a higher biological activity, the half-life may be extended by 17 times or more, thus greatly reducing the administration frequency, and meanwhile the efficacy is significantly increased.

The present application will be further described hereinafter in conjunction with drawings and specific examples, which are not intended to limit the scope of the present application. All equivalent substitutions in the art in accordance with the present application fall into the scope of the present application.

DETAILED DESCRIPTION

Figure 1:
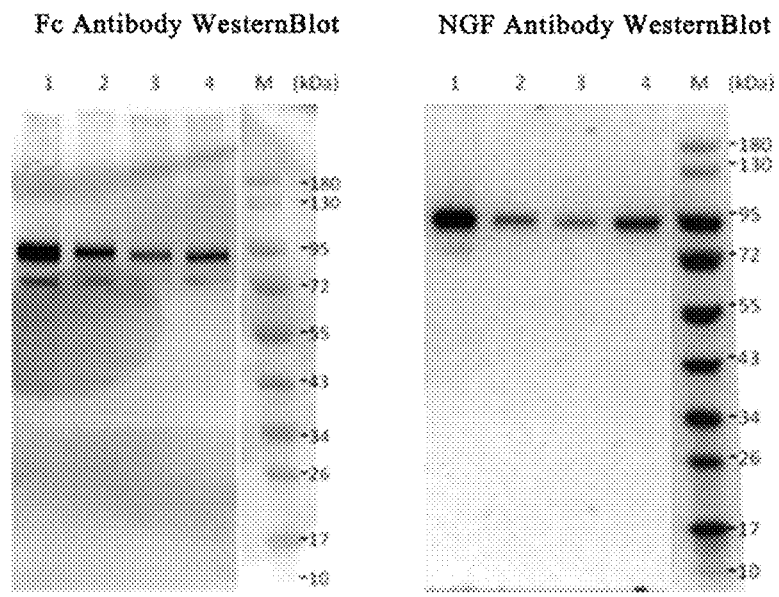
FIG. 1 is a color developing map of Western Blot of a purified sample of rhNGF-Fc fusion protein in Example 2.

The examples described hereinafter in conjunction with the drawings are illustrative, and intended to illustrate the present application, but is not to be construed as limiting the present application. The techniques or conditions not specified in the examples are performed in accordance with techniques or conditions described in the literature in the art or in accordance with the product specifications. All reagents or instruments that do not specify the manufacturer are commercially available common products.

Example 1: Preparation of Expression Plasmid of the Fusion Protein (1) Construction of Expression Plasmid of rhNGF-Fc1 Fusion Protein A nucleotide sequence SEQ ID NO: 3 encoding human β-NGF was synthesized, and amplified as a template by PCR using primers F1/R1 to obtain a NGF fragment including a Not I restriction enzyme site at the 5' end. A nucleotide sequence SEQ ID NO: 8 encoding human IgG1-Fc was synthesized and amplified as a template by PCR using primers F2/R2 to obtain an Fc fragment including the Age I restriction enzyme site at the 3' end. The PCR products of the NGF fragment and of the Fc fragment were mixed and amplified as templates by PCR using primers F1/R2 to obtain an NGF-Fc fusion gene fragment and recover the NGF-Fc fusion gene fragment. Then, the NGF-Fc fusion gene fragment and plasmid pcDNA3.1 (purchased from Invitrogen (Shanghai) Trading Co., Ltd.) were respectively subjected to double digestion with Age I and Not I, recovery, ligation and transformation to obtain an expression plasmid of pcDNA3.1-rhNGF-Fc1.

F1:
(SEQ ID No: 31)
ATTTGCGGCCGCGCCACCATGACCATGTTG.

R1:
(SEQ ID No: 32)
GAGTTTTGTCACAAGATTTGGGCTCGGCTCTTCTCACAGCCTTCCTGCTG.

F2:
(SEQ ID No: 33)
CAGCAGGAAGGCTGTGAGAAGAGCCGAGCCCAAATCTTGTGACAAAACTC.

R2:
(SEQ ID No: 34)
GATTGTCGATCATTACTAACCGGTTCATTTACCCGGGGACAGG.

(2) Construction of Expression Plasmid of rhNGF-Li-Fc1 Fusion Protein

A nucleotide sequence SEQ ID NO: 3 encoding human β-NGF was synthesized, and amplified as a template by PCR using primers F1-2/R1-2 to obtain a NGF fragment including a Not I restriction enzyme site at the 5' end. A combined sequence of a nucleotide sequence SEQ ID NO: 35 encoding a linker $(G_4S)_3$ and a nucleotide sequence SEQ ID NO: 9 encoding human IgG1-Fc was synthesized and amplified as a template by PCR using primers F2-2/R2-2 to obtain an Fc fragment including the Age I restriction enzyme site at the 3' end. The PCR products of the NGF fragment and of the Fc fragment were mixed and amplified as templates by PCR using primers F1-2/R2-2 to obtain an NGF-Fc fusion gene fragment and recover the NGF-Fc fusion gene fragment. Then, the NGF-Fc fusion gene fragment and a plasmid pcDNA3.1 (purchased from Invitrogen (Shanghai) Trading Co., Ltd.) were respectively subjected to double digestion with Age I and Not I, recovery, ligation and transformation to obtain a expression plasmid of pcDNA3.1-rhNGF-li-Fc1.

F1-2:
(SEQ ID No: 36)
GCCCTCTAGACTCGAGCGGCCGCGCCACCATGACCATGTTGT

TCTACACTC.

R1-2:
(SEQ ID No: 37)
CGCCGGAGCCGCCACCGCCGGCTCTTCTCACAGCCTTCCTG.

F2-2:
(SEQ ID No: 38)
CAGGAAGGCTGTGAGAAGAGCCGGCGGTGGCGGCTCCGGCG.

R2-2:
(SEQ ID No: 39)
GATTGTCGATCATTACTAACCGGTTCATTTACCCGGGGACAG

GGAGAGGC.

(3) Construction of Expression Plasmid of rhNGF(F12E)-Fc1 Fusion Protein

The expression plasmid of fusion protein pcDNA3.1-rhNGF-Fc1 was amplified as a template by PCR using mutant primers F12E-F/F12E-R, recovered, digested with a Dpn I restriction enzyme and then transformed, to obtain a expression plasmid of pcDNA3.1-rhNGF(F12E)-Fc1.

F12E-F:
(SEQ ID No: 40)
TTCCACAGGGGCGAAGAGTCGGTGTGTGACAGT.

F12E-R:
(SEQ ID No: 41)
ACTGTCACACACCGACTCTTCGCCCCTGTGGAA.

(4) Construction of Expression Plasmid of rhNGF-Fc4 Protein

First, the pcDNA3.1-rhNGF-Fc1 fusion gene was amplified as a template by PCR using primers 1F/1R to obtain a vector backbone containing the NGF sequence. A human IgG4-Fc nucleotide sequence SEQ ID NO: 12 was synthesized and amplified as a template by PCR using primers PAA-F/PAA-R to obtain an IgG4-Fc-containing fragment. Then, the two PCR products were seamlessly linked and then transformed.

1F:
(SEQ ID No: 42)
GTCTCTGGGTAAATAAACCGGTTAGTAATGATC

1R:
(SEQ ID No: 43)
GACCATATTTGGACTCGGCTCTTCTCACAGC.

PAA-F:
(SEQ ID No: 44)
CTGCCCAGCACCTGAGGCTGCGGGGGGACCATCAGTCTTC.

PAA-R:
(SEQ ID No: 45)
GAAGACTGATGGTCCCCCCGCAGCCTCAGGTGCTGGGCAG.

Experimental Results

Positive clones were picked up for sequencing, and the result confirmed that the gene sequences expressed by the rhNGF-Fc1, rhNGF-li-Fc1, rhNGF(F12E)-Fc1 and rhNGF-Fc4 fusion proteins were correct.

Example 2: Expression and Purification of Fusion Protein

1. CHO Cell Expressing the Fusion Protein

The cultured CHO cells were suspended, and were adjusted to a cell density of $2.5 \times 10^6$/ml after washing once with DMEM medium. Each 300 ml of cells for transfection required the following steps: 300 μg of expression plasmid was diluted with 10 ml of Opti-RPO (Invitrogen), 1.5 ml of PEI is diluted with 6 ml of Opti-PRO (1 mg/ml), after dilution they were thoroughly mixed respectively and left for 5 min. Then PEI dilution was added to the plasmid dilution, mixed and incubated for 10 min at room temperature. The PEI-plasmid mixture was then slowly added to 150 ml of resuspended cells, and incubated under shaking in a 6% carbon dioxide incubator at 37° C. and 105 rpm for 4 h. An equal volume of 150 ml of expression medium EX-CELL Advanced CHO Fed-batch medium (sigma) and 1 mM sodium valproate (0.5 mol/L) were added, and incubated under shaking in a 6% carbon dioxide incubator at 32° C. and 120 rpm for 18-24 h. 30 ml of supplement Sheff-CHO Plus ACF (Kerry Sheffield) (50 g/L) was added, and the supernatant was harvested after 4 days.

2. Purification of Fusion Protein by Protein A Affinity Column

The supernatant was collected from the cell culture, and the cells and fragments were removed by filtration through a 0.45 μm filter. The supernatant was loaded to a prepared Protein A column, purified with 20 mM PB+0.15 M NaCl solution (pH 7.2), further eluted with 50 mM citrate buffer (pH 3.4), and the protein sample was collected and immediately neutralized to a pH of 6.8 by adding 2 mol/L Tris solution.

The purified samples were subjected to Western Blot detections of NGF antibody and Fc antibody. The results are shown in FIG. 1, in which samples corresponding to lanes 1 to 4 are rhNGF-Fc1, rhNGF-li-Fc1, rhNGF(F12E)-Fc1 and rhNGF-Fc4 fusion proteins, respectively.

Example 3: Detection of In Vitro Activity of Fusion Protein

The detailed operation method was performed in accordance with the method in Example 1 of a patent entitled "Method for Quantitatively Measuring Nerve Growth Factor Activity" with a publication number of CN103376248A, and the specific activity and molar specific activity results are shown in the following table.

Figure 2:
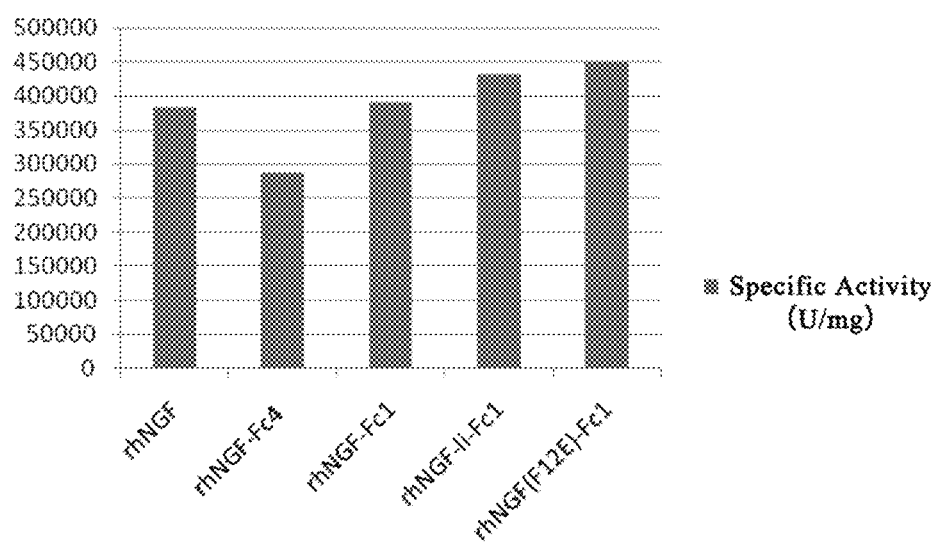
FIG. 2 is a detection result of the in vitro activity of the fusion protein in Example 3.
Figure 3:
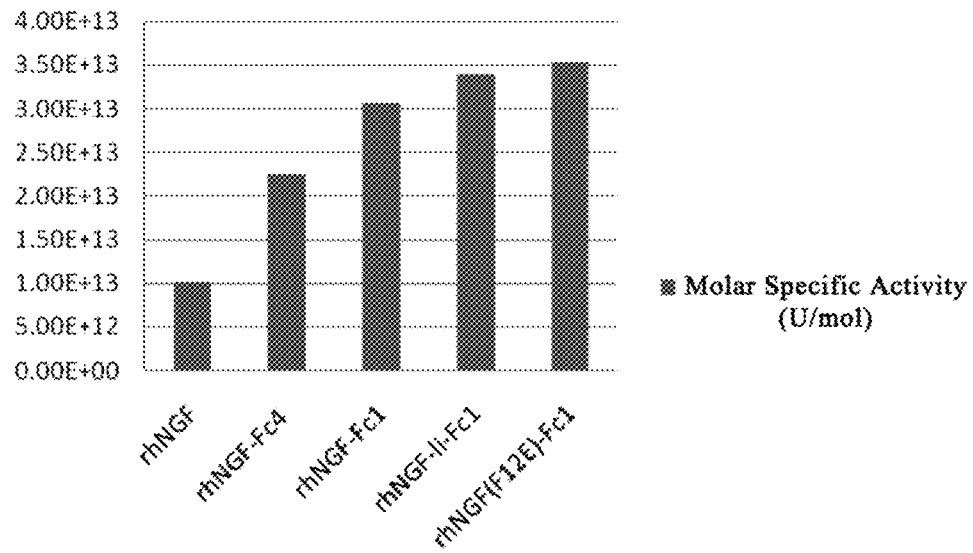
FIG. 3 is a detection result of in vitro activity of the fusion protein in Example 3.

The experimental results were shown in Table 1, FIG. 2 and FIG. 3.

The specific activity of rhNGF-Fc1, rhNGF-li-Fc1, rhNGF(F12E)-Fc1 fusion proteins was basically the same as that of rhNGF, while the specific activity of rhNGF-Fc4 fusion protein was decreased.

According to the calculation of the molar specific activity converted by molecular weight, the molar specific activity of the NGF fusion protein of the IgG1-Fc subtype was higher than that of the corresponding rhNGF, and was also better than the molar specific activity of the rhNGF-Fc4 fusion protein.

TABLE 1

| Activity | Test Sample | | | | |
|---|---|---|---|---|---|
| | rhNGF | rhNGF-Fc4 | rhNGF-Fc1 | rhNGF-li-Fc1 | rhNGF(F12E)-Fc1 |
| Specific Activity (U/mg) | 383001.55 | 286921.8 | 390443.1 | 431625 | 448338.8 |
| Molar Specific Activity (U/mol) | 1.03E+13 | 2.26E+13 | 3.07E+13 | 3.40E+13 | 3.53E+13 |

Example 4: Detection of the In Vivo Half-Life of Fusion Protein

1. Administration and Blood Collection

SD male rats weighted about 250 g were randomly divided into groups (4 rats per group), and the test samples were administered intramuscularly in a dose of 1 ml/kg according to the body weight of the rats. The test samples were rhNGF, rhNGF-Fc1, rhNGF-li-Fc1, rhNGF (F12E)-Fc1 and rhNGF-Fc4, respectively, and the dose was 1.2 nmol/kg. 0.15 ml of blood was collected from posterior orbital vein at different time points before and after administration. The collected blood was immediately placed in a 1.5 ml EP tube pre-loaded with 20 ul of 1% heparin sodium, and the mixture was immediately inverted and mixed several times, followed by centrifuge at 4000 rpm and 4° C. for 20 min. The supernatant plasma was collected and frozen at −80° C.

2. Elisa Detection

The concentration of the drug in the plasma was detected by using hNGF elisa kit (purchased from Beijing sinobiological Co., Ltd., item number: SEK11505).

3. Results

Figure 4:
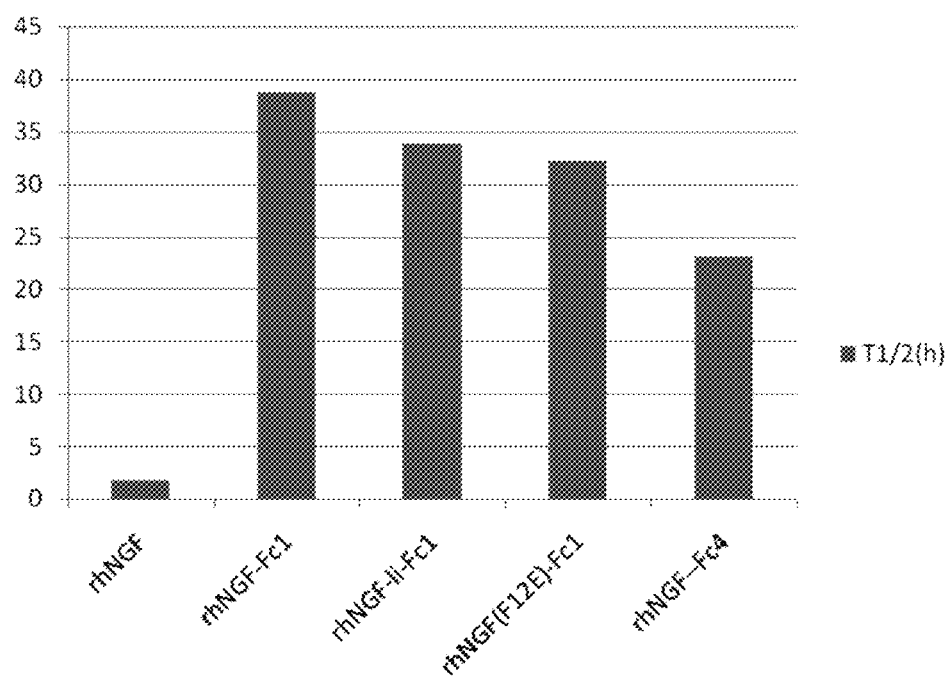
FIG. 4 is a detection result of in vivo half-life of the fusion protein in Example 4.

According to the results of the concentration of hNGF in the plasma by Elisa detection, the half-life of the test sample was fitting calculated by the non-compartmental model method (NCA) with WinNonlin 6.2 software. The obtained T1/2 of the rhNGF, rhNGF-Fc1, rhNGF-li-Fc1, rhNGF (F12E)-Fc1 and rhNGF-Fc4 proteins were 1.8h, 38.75h, 33.83h, 32.24h and 23.1h, respectively. As compared with the in vivo half-life of rhNGF of 1.8h, the in vivo half-life of the fusion proteins rhNGF-Fc1, rhNGF-li-Fc1 and rhNGF (F12E)-Fc1 was significantly prolonged, thereby achieving 32 hours or more and prolonging by more than 17 times. As compared with the in vivo half-life of rhNGF-Fc4, the in vivo half-life of the fusion proteins rhNGF-Fc1, rhNGF-li-Fc1 and rhNGF(F12E)-Fc1 were greatly prolonged, thereby reducing the metabolic rate of rhNGF. The results are shown in Table 2 and FIG. 4.

TABLE 2

| Test Sample | $T_{1/2}(h)$ |
|---|---|
| rhNGF | 1.8 |
| rhNGF-Fc1 | 38.75 |
| rhNGF-li-Fc1 | 33.83 |
| rhNGF(F12E)-Fc1 | 32.24 |
| rhNGF--Fc4 | 23.1 |

Example 5: Detection of Efficacy of Fusion Protein

Male Kunming mice were selected, and the pain threshold (basal pain threshold, taking the licking rear feet as an observational indication) was determined by hot plate method (54-55° C.), and male Kunming mice with a pain threshold of more than 30s were excluded, to obtain eligible mice. Mouse was anesthetized with ether, and then a mouse model of sciatic nerve injury using a nerve clamping method was established, while the sham operation group was only separated the sciatic nerve, but without a clamp.

Mice were divided into three groups: a sham operation group, an injury control group (normal saline) and an experimental group (rhNGF, rhNGF-Fc1, rhNGF-li-Fc1, rhNGF(F12E)-Fc1 and rhNGF-Fc4 fusion proteins), in which each group includes 5 mice.

During the operation, 50 μl of protein sample having the corresponding concentration or normal saline (control) was topically added dropwise, the skin was sutured; 0.5E+11 AU/mol of protein sample or normal saline was intraperitoneally injected to the mice, and the pain threshold of each mouse (the latency of the licking rear feet of the mouse, i.e., the pain threshold (s)) was determined before the surgery and on day 1, day 3, day 5 and day 10 after the surgery, respectively.

According to the pain threshold, the increase in pain threshold of the mouse on day 10 was calculated according to the following formula:

$$\text{Increase in pain threshold } (\%) = \frac{\text{Pain threshold on day 10 after injury} - \text{Pain threshold before injury}}{\text{Pain threshold before injury}} \times 100\%$$

The experimental results are shown in Table 3 below. As can be seen from the pain threshold value, the pain threshold of the sciatic nerve injured mouse increased on day 1 to day 3 significantly, and the pain threshold gradually recovered over time. The increase in pain threshold of the NGF fusion protein sample of IgG1-Fc and IgG4-Fc subtypes on day 10 after a single-dose administration was significantly better than those of the rhNGF group and the injury control group, and the recovery effect of the NGF fusion protein of IgG1-Fc subtype was significantly better than that of the fusion protein of IgG4-Fc subtype.

TABLE 3

Effect of Fusion Protein on Pain Threshold Changes in Mouse After Sciatic Nerve Injury

| Experimental Treatments (AU/mol) | Before Injury (s) | After Injury (s) | | | | Increase in Pain Threshold on Day 10 (%) |
|---|---|---|---|---|---|---|
| | | 1 d | 3 d | 5 d | 10 d | |
| Sham Operation Group | 15.2 | 18.6 | 17.5 | 18.4 | 18.7 | 0 |
| Injury Control Group | 17.3 | 56.8 | 57.4 | 51.9 | 36.5 | 111.0 |
| rhNGF | 17.1 | 48.8 | 54.6 | 47.5 | 33.9 | 98.2 |
| rhNGF-Fc1 | 17.0 | 59.7 | 56.4 | 44.2 | 27.1 | 59.4 |
| rhNGF-li-Fc1 | 16.9 | 55.7 | 57.1 | 48.6 | 29.4 | 60.4 |
| rhNGF(F12E)-Fc1 | 15.8 | 54.2 | 51.7 | 44.5 | 25.3 | 60.1 |
| rhNGF--Fc4 | 18.6 | 60.1 | 53.9 | 50.1 | 32.1 | 72.6 |

What is claimed is:

1. A nerve growth factor fusion protein, comprising a general formula A-B or A-L-B, wherein:
   A is a human nerve growth factor,
   L is a linker peptide, and
   B is an Fc moiety of IgG1, a mutant of the Fc moiety of IgG1, or a fragment of the Fc moiety of IgG1, wherein the mutant of the Fc moiety comprises a site mutation associated with antibody dependent cell-mediated cytotoxicity (ADCC)/complement dependent cytotoxicity (CDC) activity, or a deglycosylation mutation;
   wherein the human nerve growth factor comprises F12E with reference to the amino acid position set forth in mature wild-type human nerve growth factor.

2. The nerve growth factor fusion protein according to claim 1, wherein the mutant of Fc moiety of IgG1 has an amino acid sequence of SEQ ID NO: 7, or an amino acid sequence of SEQ ID NO: 7 with the first 5 amino acids deleted at the N-terminus.

3. The nerve growth factor fusion protein according to claim 1, wherein the nerve growth factor comprises an amino acid sequence of SEQ ID NO: 2.

4. The nerve growth factor fusion protein according to claim 1, wherein L is a glycine-rich peptide or a peptide having a sequence [SEQ ID NO: 46]n, wherein n is 1, 2, 3, 4, 5 or 6.

5. The nerve growth factor fusion protein according to claim 1, wherein L is not more than 30 amino acids in length.

6. The nerve growth factor fusion protein according to claim 1, wherein the nerve growth factor fusion protein comprises an amino acid sequence of SEQ ID NO: 10.

7. A pharmaceutical composition, comprising a pharmaceutically acceptable excipient, and a nerve growth factor fusion protein; wherein the nerve growth factor fusion protein comprises a general formula A-B or A-L-B, wherein A is a human nerve growth factor, L is a linker peptide, and B is an Fc moiety of IgG1, a mutant of the Fc moiety of IgG1, or a fragment of the Fc moiety of IgG1, wherein the mutant of the Fc moiety comprises a site mutation associated with antibody dependent cell-mediated cytotoxicity (ADCC)/complement dependent cytotoxicity (CDC) activity, or a deglycosylation mutation:
   wherein the human nerve growth factor comprises F12E with reference to the amino acid position set forth in mature wild-type human nerve growth factor.

8. The pharmaceutical composition according to claim 7, wherein the pharmaceutical composition is an injection comprising a pharmaceutically acceptable excipient and a nerve growth factor fusion protein.

9. The pharmaceutical composition according to claim 7, wherein the mutant of Fc moiety of IgG1 has an amino acid sequence of SEQ ID NO: 7, or an amino acid sequence of SEQ ID NO: 7 with the first 5 amino acids deleted at the N-terminus.

* * * * *

SEQUENCE LISTING

<160> NUMBER OF SEQ ID NOS: 47

<210> SEQ ID NO 1
<211> LENGTH: 241
<212> TYPE: PRT
<213> ORGANISM: Homo sapiens

<400> SEQUENCE: 1

```
Met Thr Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 2

<211> LENGTH: 241
<212> TYPE: PRT
<213> ORGANISM: Homo sapiens

<400> SEQUENCE: 2

```
Met Thr Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser His Pro Ile Phe
        115                 120                 125

His Arg Gly Glu Glu Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 3
<211> LENGTH: 723
<212> TYPE: DNA
<213> ORGANISM: Homo sapiens

<400> SEQUENCE: 3

```
atgaccatgt tgttctacac tctgatcaca gcttttctga tcggcataca ggcggaacca      60
cactcagaga gcaatgtccc tgcaggacac accatccccc aagtccactg gactaaactt     120
cagcattccc ttgacactgc ccttcgcaga gcccgcagcg ccccggcagc ggcgatagct     180
gcacgcgtgg cggggcagac cgcaacatt actgtggacc ccaggctgtt taaaaagcgg     240
cgactccgtt caccccgtgt gctgtttagc acccagcctc cccgtgaagc tgcagacact     300
caggatctgg acttcgaggt cggtggtgct gccccttca acaggactca aggagcaag     360 cggtcatcat cccatcccat cttccacagg ggcgaattct cggtgtgtga cagtgtcagc     420
gtgtgggttg gggataagac caccgccaca gacatcaagg gcaaggaggt gatggtgttg     480
ggagaggtga acattaacaa cagtgtattc aaacagtact ttttgagac caagtgccgg     540
```

```
gacccaaatc cgttgacag cgggtgccgg ggcattgact caaagcactg gaactcatat    600
tgtaccacga ctcacacctt tgtcaaggcg ctgaccatgg atggcaagca ggctgcctgg    660
cggtttatcc ggatagatac ggcctgtgtg tgtgtgctca gcaggaaggc tgtgagaaga    720
gcc                                                                  723
```

<210> SEQ ID NO 4
<211> LENGTH: 723
<212> TYPE: DNA
<213> ORGANISM: Homo sapiens

<400> SEQUENCE: 4

```
atgaccatgt tgttctacac tctgatcaca gcttttctga tcggcataca ggcggaacca     60
cactcagaga gcaatgtccc tgcaggacac accatccccc aagtccactg gactaaactt    120
cagcattccc ttgacactgc ccttcgcaga gcccgcagcg ccccggcagc ggcgatagct    180
gcacgcgtgg cggggcagac ccgcaacatt actgtggacc ccaggctgtt taaaaagcgg    240
cgactccgtt caccccgtgt gctgtttagc acccagcctc cccgtgaagc tgcagacact    300
caggatctgg acttcgaggt cggtggtgct gccccttca acaggactca caggagcaag    360
cggtcatcat cccatcccat cttccacagg ggcgaagagt cggtgtgtga cagtgtcagc    420
gtgtgggttg gggataagac caccgccaca gacatcaagg gcaaggaggt gatggtgttg    480
ggagaggtga acattaacaa cagtgtattc aaacagtact ttttgagac caagtgccgg    540 gacccaaatc cgttgacag cgggtgccgg ggcattgact caaagcactg gaactcatat    600
tgtaccacga ctcacacctt tgtcaaggcg ctgaccatgg atggcaagca ggctgcctgg    660
cggtttatcc ggatagatac ggcctgtgtg tgtgtgctca gcaggaaggc tgtgagaaga    720
gcc                                                                  723
```

<210> SEQ ID NO 5
<211> LENGTH: 232
<212> TYPE: PRT
<213> ORGANISM: Homo sapiens

<400> SEQUENCE: 5

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 699
<212> TYPE: DNA
<213> ORGANISM: Homo sapiens

<400> SEQUENCE: 6
gagcccaaat cttgtgacaa aactcacaca tgcccaccgt gcccagcacc tgaactcctg      60
gggggaccgt cagtcttcct cttcccccca aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gaggagatga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgacgg ctccttcttc ctctatagca agctcaccgt ggacaagagc     600
aggtggcagc aggggaacgt cttctcatgc tccgtgatgc atgaggctct gcacaaccac     660
tacacgcaga agagcctctc cctgtccccg ggtaaatga                            699

<210> SEQ ID NO 7
<211> LENGTH: 231
<212> TYPE: PRT
<213> ORGANISM: Homo sapiens

<400> SEQUENCE: 7

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125
```

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 8
<211> LENGTH: 696
<212> TYPE: DNA
<213> ORGANISM: Homo sapiens

<400> SEQUENCE: 8
gagcccaaat cttgtgacaa aactcacaca tgcccaccgt gcccagcacc tccagtcgca      60
ggaccgtcag tcttcctctt ccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gcctcccat cctccatcga gaaaaccatc      360
tccaaagcca aagggcagcc ccgagaacca caggtgtaca ccctgccccc atcccgggag     420
gagatgacca agaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tatagcaagc tcaccgtgga caagagcagg     600
tggcagcagg ggaacgtctt ctcatgctcc gtgatgcatg aggctctgca caaccactac     660
acgcagaaga gcctctccct gtccccgggt aaatga                               696

<210> SEQ ID NO 9
<211> LENGTH: 681
<212> TYPE: DNA
<213> ORGANISM: Homo sapiens

<400> SEQUENCE: 9
gacaaaactc acacatgccc accgtgccca gcacctccag tcgcaggacc gtcagtcttc      60
ctcttccccc caaaacccaa ggacaccctc atgatctccc ggaccctga ggtcacatgc      120 gtggtggtgg acgtgagcca cgaagaccct gaggtcaagt tcaactggta cgtggacggc     180
gtggaggtgc ataatgccaa gacaaagccg cgggaggagc agtacaacag cacgtaccgt     240
gtggtcagcg tcctcaccgt cctgcaccag gactggctga atggcaagga gtacaagtgc     300
aaggtctcca acaaaggcct cccatcctcc atcgagaaaa ccatctccaa agccaaaggg     360
cagccccgag aaccacaggt gtacaccctg ccccatccc gggaggagat gaccaagaac      420
caggtcagcc tgacctgcct ggtcaaaggc ttctatccca gcgacatcgc cgtggagtgg     480
gagagcaatg gcagccgga gaacaactac aagaccacgc ctcccgtgct ggactccgac      540

```
ggctccttct tcctctatag caagctcacc gtggacaaga gcaggtggca gcagggggaac    600 gtcttctcat gctccgtgat gcatgaggct ctgcacaacc actacacgca aagagcctc     660 tccctgtccc cgggtaaatg a                                               681
```

<210> SEQ ID NO 10
<211> LENGTH: 482
<212> TYPE: PRT
<213> ORGANISM: Homo sapiens

<400> SEQUENCE: 10

```
Met Thr Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Glu Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala Gly Gly Gly Ser Gly Gly Gly Ser Gly Gly Gly Ser
                245                 250                 255

Asp Lys Thr His Thr Cys Pro Pro Cys Pro Ala Pro Pro Val Ala Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
```

```
                340              345              350
Glu Tyr Lys Cys Lys Val Ser Asn Lys Gly Leu Pro Ser Ser Ile Glu
            355                      360                      365

Lys Thr Ile Ser Lys Ala Lys Gly Gln Pro Arg Glu Pro Gln Val Tyr
    370                      375                      380

Thr Leu Pro Pro Ser Arg Glu Glu Met Thr Lys Asn Gln Val Ser Leu
385                      390                      395                      400

Thr Cys Leu Val Lys Gly Phe Tyr Pro Ser Asp Ile Ala Val Glu Trp
                    405                      410                      415

Glu Ser Asn Gly Gln Pro Glu Asn Asn Tyr Lys Thr Thr Pro Pro Val
                420                      425                      430

Leu Asp Ser Asp Gly Ser Phe Phe Leu Tyr Ser Lys Leu Thr Val Asp
            435                      440                      445

Lys Ser Arg Trp Gln Gln Gly Asn Val Phe Ser Cys Ser Val Met His
        450                      455                      460

Glu Ala Leu His Asn His Tyr Thr Gln Lys Ser Leu Ser Leu Ser Pro
465                      470                      475                      480

Gly Lys

<210> SEQ ID NO 11
<211> LENGTH: 1449
<212> TYPE: DNA
<213> ORGANISM: Homo sapiens

<400> SEQUENCE: 11
atgaccatgt tgttctacac tctgatcaca gcttttctga tcggcataca ggcggaacca      60
cactcagaga gcaatgtccc tgcaggacac accatccccc aagtccactg gactaaactt     120
cagcattccc ttgacactgc ccttcgcaga gcccgcagcg ccccggcagc ggcgatagct     180
gcacgcgtgg cggggcagac cgcaacatt  actgtggacc ccaggctgtt taaaaagcgg     240
cgactccgtt caccccgtgt gctgtttagc acccagcctc cccgtgaagc tgcagacact     300
caggatctgg acttcgaggt cggtggtgct gccccttca  acaggactca caggagcaag     360
cggtcatcat cccatcccat cttccacagg ggcgaagagt cggtgtgtga cagtgtcagc     420
gtgtgggttg gggataagac caccgccaca gacatcaagg caaggaggt  gatggtgttg     480 ggagaggtga acattaacaa cagtgtattc aaacagtact tttttgagac caagtgccgg     540
gacccaaatc ccgttgacag cgggtgccgg ggcattgact caaagcactg gaactcatat     600
tgtaccacga ctcacacctt tgtcaaggcg ctgaccatgg atggcaagca ggctgcctgg     660
cggtttatcc ggatagatac ggcctgtgtg tgtgtgctca gcaggaaggc tgtgagaaga     720
gccggcggtg cgggctccgg cggtggcggc tccggcggtg cgggctccga caaaactcac     780
acatgcccac cgtgcccagc acctccagtc gcaggaccgt cagtcttcct cttcccccca     840
aaacccaagg acaccctcat gatctcccgg acccctgagg tcacatgcgt ggtggtggac     900
gtgagccacg aagaccctga ggtcaagttc aactggtacg tggacggcgt ggaggtgcat     960
aatgccaaga caaagccgcg ggaggagcag tacaacagca cgtaccgtgt ggtcagcgtc    1020
ctcaccgtcc tgcaccagga ctggctgaat ggcaaggagt acaagtgcaa ggtctccaac    1080
aaaggcctcc catcctccat cgagaaaacc atctccaaag ccaagggca  gccccgagaa    1140 ccacaggtgt acaccctgcc cccatcccgg gaggagatga ccaagaacca ggtcagcctg    1200
acctgcctgg tcaaaggctt ctatcccagc gacatcgccg tggagtggga gagcaatggg    1260
cagccggaga acaactacaa gaccacgcct cccgtgctgg actccgacgg ctccttcttc    1320
```

```
ctctatagca agctcaccgt ggacaagagc aggtggcagc aggggaacgt cttctcatgc    1380
tccgtgatgc atgaggctct gcacaaccac tacacgcaga gagcctctc cctgtccccg    1440 ggtaaatga                                                             1449
```

<210> SEQ ID NO 12
<211> LENGTH: 690
<212> TYPE: DNA
<213> ORGANISM: Homo sapiens

<400> SEQUENCE: 12

```
gagtccaaat atggtccccc atgcccaccc tgcccagcac ctgaggctgc gggggggacca     60 tcagtcttcc tgttcccccc aaaacccaag gacactctca tgatctcccg gaccccctgag   120 gtcacgtgcg tggtggtgga cgtgagccag gaagacccg aggtccagtt caactggtac    180
gtggatggcg tggaggtgca taatgccaag acaaagccgc gggaggagca gttcaacagc   240
acgtaccgtg tggtcagcgt cctcaccgtc ctgcaccagg actggctgaa cggcaaggag   300
tacaagtgca aggtctccaa caaaggcctc ccgtcctcca tcgagaaaac catctccaaa   360
gccaaagggc agccccgaga gccacaggtg tacaccctgc ccccatccca ggaggagatg    420
accaagaacc aggtcagcct gacctgcctg gtcaaaggct tctacccag cgacatcgcc    480 gtggagtggg aaagcaatgg gcagccggag aacaactaca agaccacgcc tcccgtgctg    540
gactccgacg gctccttctt cctctacagc aggctaaccg tggacaagag caggtggcag    600
gagggaaatg tcttctcatg ctccgtgatg catgaggctc tgcacaacca ctacacacag    660
aagagcctct ccctgtctct gggtaaataa                                     690
```

<210> SEQ ID NO 13
<211> LENGTH: 120
<212> TYPE: PRT
<213> ORGANISM: Homo sapiens

<400> SEQUENCE: 13

```
Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Gly
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120
```

<210> SEQ ID NO 14
<211> LENGTH: 120
<212> TYPE: PRT
<213> ORGANISM: Homo sapiens

<400> SEQUENCE: 14

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Leu
            20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Arg Asp Pro Asn Pro Val
        50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 15
<211> LENGTH: 120
<212> TYPE: PRT
<213> ORGANISM: Homo sapiens

<400> SEQUENCE: 15

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Tyr
            20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Arg Asp Pro Asn Pro Val
        50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 16
<211> LENGTH: 120
<212> TYPE: PRT
<213> ORGANISM: Homo sapiens

<400> SEQUENCE: 16

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Leu Asp Pro Asn Pro Val
        50                  55                  60

Asp Ser Gly Cys Arg Gly Ile Asp Ser Lys His Trp Asn Ser Tyr Cys
65                  70                  75                  80

```
Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
        100                 105                 110

Ser Arg Lys Ala Val Arg Ala
        115             120

<210> SEQ ID NO 17
<211> LENGTH: 120
<212> TYPE: PRT
<213> ORGANISM: Homo sapiens

<400> SEQUENCE: 17

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Ala Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
        100                 105                 110

Ser Arg Lys Ala Val Arg Ala
        115             120

<210> SEQ ID NO 18
<211> LENGTH: 120
<212> TYPE: PRT
<213> ORGANISM: Homo sapiens

<400> SEQUENCE: 18

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Ala Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
        100                 105                 110

Ser Arg Lys Ala Val Arg Ala
        115             120

<210> SEQ ID NO 19
<211> LENGTH: 120
<212> TYPE: PRT
<213> ORGANISM: Homo sapiens
```

<400> SEQUENCE: 19

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Gly Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 20
<211> LENGTH: 120
<212> TYPE: PRT
<213> ORGANISM: Homo sapiens

<400> SEQUENCE: 20

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Leu His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 21
<211> LENGTH: 120
<212> TYPE: PRT
<213> ORGANISM: Homo sapiens

<400> SEQUENCE: 21

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys

```
                65                  70                  75                  80
Thr Thr Thr His Thr Phe Val Phe Ala Leu Thr Met Asp Gly Lys Gln
                    85                  90                  95
Ala Ala Trp Arg Phe Ile Arg Ile Asp Thr Ala Cys Val Cys Val Leu
            100                 105                 110
Ser Arg Lys Ala Val Arg Arg Ala
            115                 120

<210> SEQ ID NO 22
<211> LENGTH: 120
<212> TYPE: PRT
<213> ORGANISM: Homo sapiens

<400> SEQUENCE: 22

Ser Ser Ser His Pro Ile Phe His Arg Gly Glu Phe Ser Val Cys Asp
1               5                   10                  15
Ser Val Ser Val Trp Val Gly Asp Lys Thr Thr Ala Thr Asp Ile Lys
            20                  25                  30
Gly Lys Glu Val Met Val Leu Gly Glu Val Asn Ile Asn Asn Ser Val
            35                  40                  45
Phe Lys Gln Tyr Phe Phe Glu Thr Lys Cys Arg Asp Pro Asn Pro Val
        50                  55                  60
Asp Ser Gly Cys Arg Gly Ile Asp Ser Lys His Trp Asn Ser Tyr Cys
65                  70                  75                  80
Thr Thr Thr His Thr Phe Val Leu Ala Leu Thr Met Asp Gly Lys Gln
                    85                  90                  95
Ala Ala Trp Arg Phe Ile Arg Ile Asp Thr Ala Cys Val Cys Val Leu
            100                 105                 110
Ser Arg Lys Ala Val Arg Arg Ala
            115                 120

<210> SEQ ID NO 23
<211> LENGTH: 120
<212> TYPE: PRT
<213> ORGANISM: Homo sapiens

<400> SEQUENCE: 23

Ser Ser Ser His Pro Ile Phe His Arg Gly Glu Phe Ser Val Cys Asp
1               5                   10                  15
Ser Val Ser Val Trp Val Gly Asp Lys Thr Thr Ala Thr Asp Ile Lys
            20                  25                  30
Gly Lys Glu Val Met Val Leu Gly Glu Val Asn Ile Asn Asn Ser Val
            35                  40                  45
Phe Lys Gln Tyr Phe Phe Glu Thr Lys Cys Arg Asp Pro Asn Pro Val
        50                  55                  60
Asp Ser Gly Cys Arg Gly Ile Asp Ser Lys His Trp Asn Ser Tyr Cys
65                  70                  75                  80
Thr Thr Thr His Thr Phe Val Glu Ala Leu Thr Met Asp Gly Lys Gln
                    85                  90                  95
Ala Ala Trp Arg Phe Ile Arg Ile Asp Thr Ala Cys Val Cys Val Leu
            100                 105                 110
Ser Arg Lys Ala Val Arg Arg Ala
            115                 120

<210> SEQ ID NO 24
<211> LENGTH: 120
<212> TYPE: PRT
```

<213> ORGANISM: Homo sapiens

<400> SEQUENCE: 24

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Gly Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 25
<211> LENGTH: 120
<212> TYPE: PRT
<213> ORGANISM: Homo sapiens

<400> SEQUENCE: 25

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Glu
                85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 26
<211> LENGTH: 120
<212> TYPE: PRT
<213> ORGANISM: Homo sapiens

<400> SEQUENCE: 26

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

```
Asp Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
             85                  90                  95

Ala Ala Trp Arg Phe Ile Arg Ile Asp Thr Ala Cys Val Cys Val Leu
            100                 105                 110

Ser Val Lys Ala Val Arg Arg Ala
            115                 120

<210> SEQ ID NO 27
<211> LENGTH: 120
<212> TYPE: PRT
<213> ORGANISM: Homo sapiens

<400> SEQUENCE: 27

Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
                20                  25                  30

Gly Lys Glu Val Met Val Leu Gly Glu Val Asn Ile Asn Asn Ser Val
             35                  40                  45

Phe Lys Gln Tyr Phe Phe Glu Thr Lys Cys Arg Asp Pro Asn Pro Val
 50                  55                  60

Asp Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
             85                  90                  95

Ala Ala Trp Arg Phe Ile Arg Ile Asp Thr Ala Cys Val Cys Val Leu
            100                 105                 110

Ser Phe Lys Ala Val Arg Arg Ala
            115                 120

<210> SEQ ID NO 28
<211> LENGTH: 120
<212> TYPE: PRT
<213> ORGANISM: Homo sapiens

<400> SEQUENCE: 28

Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
                20                  25                  30

Gly Lys Glu Val Met Val Leu Gly Glu Val Asn Ile Asn Asn Ser Val
             35                  40                  45

Phe Lys Gln Tyr Phe Phe Glu Thr Lys Cys Arg Asp Pro Asn Pro Val
 50                  55                  60

Asp Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
             85                  90                  95

Ala Ala Trp Arg Phe Ile Arg Ile Asp Thr Ala Cys Val Cys Val Leu
            100                 105                 110

Ser Gly Lys Ala Val Arg Arg Ala
            115                 120

<210> SEQ ID NO 29
```

```
<211> LENGTH: 120
<212> TYPE: PRT
<213> ORGANISM: Homo sapiens

<400> SEQUENCE: 29

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Leu Lys Ala Val Arg Arg Ala
        115                 120

<210> SEQ ID NO 30
<211> LENGTH: 120
<212> TYPE: PRT
<213> ORGANISM: Homo sapiens

<400> SEQUENCE: 30

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Ala Ile Arg Ile Asp Thr Ala Cys Val Cys Val Leu
            100                 105                 110

Ser Arg Lys Ala Val Arg Arg Ala
        115                 120

<210> SEQ ID NO 31
<211> LENGTH: 30
<212> TYPE: DNA
<213> ORGANISM: Artificial sequence
<220> FEATURE:
<223> OTHER INFORMATION: Primer F1

<400> SEQUENCE: 31
atttgcggcc gcgccaccat gaccatgttg                              30

<210> SEQ ID NO 32
<211> LENGTH: 50
<212> TYPE: DNA
<213> ORGANISM: Artificial sequence
```

<220> FEATURE:
<223> OTHER INFORMATION: Primer R2

<400> SEQUENCE: 32
gagttttgtc acaagatttg ggctcggctc ttctcacagc cttcctgctg    50

<210> SEQ ID NO 33
<211> LENGTH: 50
<212> TYPE: DNA
<213> ORGANISM: Artificial sequence
<220> FEATURE:
<223> OTHER INFORMATION: Primer F2

<400> SEQUENCE: 33
cagcaggaag gctgtgagaa gagccgagcc caaatcttgt gacaaaactc    50

<210> SEQ ID NO 34
<211> LENGTH: 43
<212> TYPE: DNA
<213> ORGANISM: Artificial sequence
<220> FEATURE:
<223> OTHER INFORMATION: Primer R2

<400> SEQUENCE: 34
gattgtcgat cattactaac cggttcattt acccggggac agg    43

<210> SEQ ID NO 35
<211> LENGTH: 45
<212> TYPE: DNA
<213> ORGANISM: Artificial sequence
<220> FEATURE:
<223> OTHER INFORMATION: Linker

<400> SEQUENCE: 35
ggcggtggcg gctccggcgg tggcggctcc ggcggtggcg gctcc    45

<210> SEQ ID NO 36
<211> LENGTH: 51
<212> TYPE: DNA
<213> ORGANISM: Artificial sequence
<220> FEATURE:
<223> OTHER INFORMATION: Primer F1-2

<400> SEQUENCE: 36
gccctctaga ctcgagcggc cgcgccacca tgaccatgtt gttctacact c    51

<210> SEQ ID NO 37
<211> LENGTH: 41
<212> TYPE: DNA
<213> ORGANISM: Artificial sequence
<220> FEATURE:
<223> OTHER INFORMATION: Primer R1-2

<400> SEQUENCE: 37
cgccggagcc gccaccgccg gctcttctca cagccttcct g    41

<210> SEQ ID NO 38
<211> LENGTH: 41
<212> TYPE: DNA
<213> ORGANISM: Artificial sequence
<220> FEATURE:
<223> OTHER INFORMATION: Primer F2-2

<400> SEQUENCE: 38
caggaaggct gtgagaagag ccggcggtgg cggctccggc g    41

<210> SEQ ID NO 39
<211> LENGTH: 50
<212> TYPE: DNA
<213> ORGANISM: Artificial sequence
<220> FEATURE:
<223> OTHER INFORMATION: Primer R2-2

<400> SEQUENCE: 39
gattgtcgat cattactaac cggttcattt acccggggac agggagaggc        50

<210> SEQ ID NO 40
<211> LENGTH: 33
<212> TYPE: DNA
<213> ORGANISM: Artificial sequence
<220> FEATURE:
<223> OTHER INFORMATION: Primer F12E-F

<400> SEQUENCE: 40
ttccacaggg gcgaagagtc ggtgtgtgac agt                          33

<210> SEQ ID NO 41
<211> LENGTH: 33
<212> TYPE: DNA
<213> ORGANISM: Artificial sequence
<220> FEATURE:
<223> OTHER INFORMATION: Primer F12E-R

<400> SEQUENCE: 41
actgtcacac accgactctt cgcccctgtg gaa                          33

<210> SEQ ID NO 42
<211> LENGTH: 33
<212> TYPE: DNA
<213> ORGANISM: Artificial sequence
<220> FEATURE:
<223> OTHER INFORMATION: Primer 1F

<400> SEQUENCE: 42
gtctctgggt aaataaaccg gttagtaatg atc                          33

<210> SEQ ID NO 43
<211> LENGTH: 31
<212> TYPE: DNA
<213> ORGANISM: Artificial sequence
<220> FEATURE:
<223> OTHER INFORMATION: Primer 1R

<400> SEQUENCE: 43
gaccatattt ggactcggct cttctcacag c                            31

<210> SEQ ID NO 44
<211> LENGTH: 40
<212> TYPE: DNA
<213> ORGANISM: Artificial sequence
<220> FEATURE:
<223> OTHER INFORMATION: Primer PAA-F

<400> SEQUENCE: 44
ctgcccagca cctgaggctg cgggggggacc atcagtcttc                  40

<210> SEQ ID NO 45
<211> LENGTH: 40
<212> TYPE: DNA
<213> ORGANISM: Artificial sequence
<220> FEATURE:
<223> OTHER INFORMATION: Primer PAA-R

```
<400> SEQUENCE: 45
gaagactgat ggtcccccg cagcctcagg tgctgggcag                              40

<210> SEQ ID NO 46
<211> LENGTH: 5
<212> TYPE: PRT
<213> ORGANISM: Artificial sequence
<220> FEATURE:
<223> OTHER INFORMATION: Linker peptide

<400> SEQUENCE: 46

Gly Gly Gly Gly Ser
1               5

<210> SEQ ID NO 47
<211> LENGTH: 15
<212> TYPE: PRT
<213> ORGANISM: Artificial sequence
<220> FEATURE:
<223> OTHER INFORMATION: Linker peptide

<400> SEQUENCE: 47

Gly Gly Gly Gly Ser Gly Gly Gly Gly Ser Gly Gly Gly Gly Ser
1               5                   10                  15
```